United States Patent
New

(10) Patent No.: US 9,987,232 B2
(45) Date of Patent: Jun. 5, 2018

(54) DISSOLUTION AIDS FOR ORAL PEPTIDE DELIVERY COMPRISING A BIGUANIDE

(75) Inventor: Roger R. C. New, London (GB)

(73) Assignee: Axcess Limited, Jersey (GB)

( * ) Notice: Subject to any disclaimer, the term of this patent is extended or adjusted under 35 U.S.C. 154(b) by 567 days.

(21) Appl. No.: 13/414,829

(22) Filed: Mar. 8, 2012

(65) Prior Publication Data

US 2012/0177602 A1    Jul. 12, 2012

Related U.S. Application Data

(62) Division of application No. 12/279,806, filed as application No. PCT/GB2007/000539 on Feb. 16, 2007, now abandoned.

(30) Foreign Application Priority Data

Feb. 17, 2006   (GB) .................................. 0603252.8

(51) Int. Cl.

| | |
|---|---|
| A61K 9/48 | (2006.01) |
| A61K 31/155 | (2006.01) |
| A61K 31/192 | (2006.01) |
| A61K 31/7088 | (2006.01) |
| A61K 31/715 | (2006.01) |
| A61K 31/05 | (2006.01) |
| A61K 38/28 | (2006.01) |
| A61K 45/06 | (2006.01) |
| A61K 47/10 | (2017.01) |
| A61K 47/14 | (2017.01) |
| A61K 38/23 | (2006.01) |

(52) U.S. Cl.
CPC .......... *A61K 9/4858* (2013.01); *A61K 9/4891* (2013.01); *A61K 31/05* (2013.01); *A61K 31/155* (2013.01); *A61K 31/192* (2013.01); *A61K 31/7088* (2013.01); *A61K 31/715* (2013.01); *A61K 38/23* (2013.01); *A61K 38/28* (2013.01); *A61K 45/06* (2013.01); *A61K 47/10* (2013.01); *A61K 47/14* (2013.01)

(58) Field of Classification Search
None
See application file for complete search history.

(56) References Cited

U.S. PATENT DOCUMENTS

| | | |
|---|---|---|
| 3,996,355 A | 12/1976 | Lin et al. |
| 5,342,625 A | 8/1994 | Hauer et al. |
| 5,756,450 A | 5/1998 | Hahn et al. |
| 6,261,844 B1 | 7/2001 | Smith et al. |
| 6,803,357 B1 * | 10/2004 | Bachovchin et al. ......... 514/6.9 |
| 9,238,074 B2 * | 1/2016 | Dhoot .................. C07C 235/60 |
| 2004/0028736 A1 | 2/2004 | New |
| 2005/0059706 A1 | 3/2005 | Smith |
| 2010/0056425 A1 | 3/2010 | New |

FOREIGN PATENT DOCUMENTS

| | | |
|---|---|---|
| EP | 0 029 541 A1 | 11/1980 |
| WO | WO 02/22158 A1 | 3/2002 |
| WO | WO 2004/091584 A1 | 10/2004 |
| WO | WO 2004/091667 A1 | 10/2004 |
| WO | WO 2005/011663 A1 | 2/2005 |
| WO | WO 2005/112950 A1 | 12/2005 |
| WO | WO 2006/017541 A2 | 2/2006 |

OTHER PUBLICATIONS

International Search Report for PCT/GB2007/000539, dated Jul. 20, 2007.
Written Opinion of the International Searching Authority dated Jul. 20, 2007.
Rx List printout re Glucophage date Jan. 26, 2006.
Chemical and 21 print-out re antiseptic agent dated Feb. 13, 2006.
MedlinePlus print-out re metformin dated Jul. 26, 2005.
Additional print-outs (source unknown) regarding metformin, Leptin, Exendin-4 and Oxyntomodulin, 2012.
Handbook of Pharmaceutical Excipients, edited by Wade et al, second edition, 1994, cover sheet; "Propyl Gallate", pp. 402-404; "Butylated Hydroxytoluene", pp. 47-48; and "Butylated Hydroxyanisole", pp. 45-46.

\* cited by examiner

*Primary Examiner* — Robert A Wax
*Assistant Examiner* — Thor Nielsen
(74) *Attorney, Agent, or Firm* — Nixon & Vanderhye P.C.

(57) ABSTRACT

A pharmaceutical composition comprising a mixture of:
- (c) an active macromolecular principle;
- (d) an aromatic alcohol absorption enhancer chosen from propyl gallate, butylated hydroxy toluene (BHT), butylated hydroxy anisole (BHA) and analogs and derivatives thereof, or mixtures thereof; and
- (d) a biguanide or a pharmaceutically acceptable salt thereof, capable of increasing the solubility of the aromatic alcohol absorption enhancer in an aqueous medium, wherein the aromatic alcohol absorption enhancer is present in an amount by weight greater than or equal to that of the active principle.

17 Claims, No Drawings

DISSOLUTION AIDS FOR ORAL PEPTIDE DELIVERY COMPRISING A BIGUANIDE

This application is a divisional of application Ser. No. 12/279,806 filed Oct. 17, 2008, now abandoned which in turn is a U.S. national phase of International Application No. PCT/GB2007/000539 filed 16 Feb. 2007 which designated the U.S. and claims priority to Great Britain Application No. 0603252.8, filed 17 Feb. 2006, the entire contents of each of which are hereby incorporated by reference.

This invention relates to the use of certain aromatic alcohols as absorption enhancers to facilitate the passage of peptides, proteins and other macromolecules across the intestinal wall, and in particular, the use of new agents to aid in dissolution of said aromatic alcohols, in order to improve the availability of such agents in biological fluids, where under normal circumstances they are extremely poorly soluble.

It has previously been reported in WO 2004/091584 that aromatic alcohols such as propyl gallate, butylated hydroxy anisole and butylated hydroxy toluene can act as absorption enhancers for peptides and proteins across mucosal surfaces such as the intestine, and the action of these agents is maximized when formulated in combination with other agents which enhance their dissolution in aqueous media. Examples of such dissolution aids previously cited are bile salts such as sodium deoxycholate, and sodium chenodeoxycholate.

On the basis of the teaching from this prior art, a person skilled in the art would conclude that, in order to achieve satisfactory results, a dissolution aid needs to display surfactant activity, preferably forming micelles, as do bile salts, and indeed, one of the biological functions of bile salts in vivo is to aid the dissolution of dietary components, particularly lipids, in the intestine.

It has now been found, surprisingly, that a new and unrelated class of small molecules is also able to act as dissolution aids for poorly-soluble aromatic alcohols, in spite of the fact that these molecules display no surfactant properties, and have little tendency to form micelles. This class of small molecules is comprised of substituted biguanides, of which metformin and phenformin are typical examples.

The action of biguanides as dissolution aids appears to be specific to aromatic alcohols, and does not extend to other classes of molecules such as cholesterol or fatty acids, for which bile salts are well known as solubilising agents. Consequently, one can conclude that there is nothing about bile salts, from either a structural or a functional point of view, which would lead a skilled person to suppose that biguanides might also share their properties as dissolution aids.

Biguanides may be formulated together with poorly-soluble aromatic alcohols as excipients to yield mucosally-administered pharmaceutical formulations containing one or more active molecular principles, whose passage across the mucosal barrier is enhanced as a result of being administered in combination with the biguanide/aromatic alcohol mixture.

The invention provides a pharmaceutical composition comprising a mixture of:
(a) an active macromolecular principle; and
(b) an aromatic alcohol absorption enhancer chosen from propyl gallate, butylated hydroxy toluene, butylated hydroxy anisole and analogues and derivatives thereof, and
(c) a biguanide capable of increasing the solubility of the aromatic alcohol absorption enhancer in aqueous media, wherein the aromatic alcohol absorption enhancer is present in an amount by weight greater than or equal to that of the active macromolecular principle.

The invention also provides the use, in a pharmaceutical composition, of an aromatic alcohol chosen from propyl gallate, butylated hydroxy toluene, butylated hydroxy anisole and analogues and derivatives thereof together with a biguanide or a pharmaceutically acceptable salt thereof, capable of increasing the solubility of the aromatic alcohol in an aqueous medium as an enhancer for the absorption of macromolecules into the body.

In a further embodiment, the invention provides the use of an aromatic alcohol chosen from propyl gallate, butylated hydroxy toluene, butylated hydroxy anisole and analogues and derivatives thereof together with a biguanide or a pharmaceutically acceptable salt thereof, capable of increasing the solubility of the aromatic alcohol in an aqueous medium in the manufacture of a medicament containing an active macromolecular principle, in order to enhance absorption of the active macromolecular principle into the human or animal body.

The common feature of the series of molecules acting as dissolution aids described in this invention is the biguanide nucleus, and molecules with a variety of substitutions in the biguanide nucleus display the desired activity. In order to assess the suitability of a biguanide for use as a dissolution aid, the following procedure may be followed. Typically, a solution of the biguanide is prepared in water at a concentration of 100 mg/ml, with heating if necessary, and appropriate adjustment of pH, if a solution is not obtained immediately. To 1 ml of the solution 25 mg of propyl gallate is added, and the mixture warmed with shaking for up to half an hour. If a clear solution is obtained, the substituted biguanide may be considered suitable for use as a dissolution aid.

The biguanides for use in the present invention will suitably have the following formula

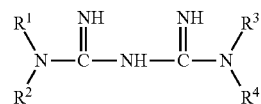

wherein $R^1$, $R^2$, $R^3$ and $R^4$ are each independently chosen from hydrogen, optionally substituted alkyl, optionally substituted phenyl, ethylene glycol, diethylene glycol, triethylene glycol and tetraethylene glycol, or one of $R^1$, $R^2$, $R^3$ and $R^4$ may be

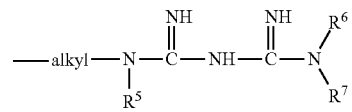

where $R^5$, $R^6$ and $R^7$ are each independently chosen from hydrogen, optionally substituted alkyl, optionally substituted phenyl, ethylene glycol, diethylene glycol, triethylene glycol and tetraethylene glycol.

Substituents for the alkyl and phenyl groups include halo, e.g. chloro, bromo, fluoro or iodo, hydroxy and amino. The alkyl groups preferably have from 1 to 6 carbons, and may be saturated or unsaturated, straight chain or branched. The biguanide may be included in the composition of the invention as a pharmaceutically acceptable salt.

Preferred biguanides for use in the present invention include metformin, phenformin and chlorhexidine or pharmaceutically acceptable salts thereof. The pharmaceutically acceptable salts are suitably the chloride, bromide, iodide or salts of organic acids such as the acetate, propionate, mesylate (methyl sulphonate) or glucuronate.

The biguanide may be present in the composition in an amount of at least 50% by weight, preferably from 60 to 95% and more preferably from 80 to 90%.

The aromatic alcohol absorption enhancer may be propyl gallate or an analogue or a derivative thereof, and, preferably is propyl gallate. Suitable analogues and derivatives of propyl gallate include esters of gallic acid. The esters may be linear or branched chain $C_{1-12}$ alkyl, $C_{1-12}$ alkyloxy, $C_{1-12}$ alkylthio or $C_{2-12}$ alkenyl esters. The compounds are optionally substituted with halogen, linear or branched chain $C_{1-12}$ alkyl, $C_{1-12}$ alkyloxy, $C_{1-12}$ alkylthio or $C_{2-12}$ alkenyl esters. The aromatic alcohol absorption enhancer may also be chosen from BHT, BHA and analogues and derivatives thereof. Suitable analogues and derivatives of BHT or BHA include analogues and derivatives of hydroxy toluene or hydroxy anisole where the methyl group or the methoxy group linked to the aromatic ring and/or the hydrogen ortho to the hydroxyl group are replaced by linear or branched chain $C_{1-12}$ alkyl, $C_{1-12}$ alkyloxy, $C_{1-12}$ alkylthio or $C_{2-12}$ alkenyl, either unsubstituted or substituted in any position, especially by halogen atoms. Preferably, the aromatic alcohol absorption enhancer is chosen from propyl gallate, BHT and BHA.

The aromatic alcohols disclosed above which are used in pharmaceutical practice as antioxidants are included at concentrations up to 0.1% w/v of the total formulation (see entries for individual compounds in the Handbook of Pharmaceutical Excipients, Eds Wade & Weller, The Pharmaceutical Press, London UK, $2^{nd}$ edition 1994). It is generally considered that higher concentrations of the compounds give no added antioxidant benefit, and it is thus standard pharmaceutical practice to restrict the concentration of the antioxidants in formulations to no greater than 0.1%. When used as absorption enhancers according to the present invention, however, the efficacy of these compounds is concentration dependent up to a much higher level, and their proportions in a pharmaceutical formulation are much higher than previously described in the prior art.

For example, WO-A-0222158 provides compositions comprising cyclosporin (not a macromolecule) and containing BHA, BHT and PG generally as antioxidants. Although no specific concentrations of the antioxidants are given, the use of the compounds as antioxidants suggests a level of no greater than 0.1% wt.

The alcohol may be present in the composition in an amount of from 5 to 30% by weight, preferably from 10 to 20%.

The active macromolecular principles falling within the scope of the invention include all molecules capable of having a beneficial effect when absorbed into the human or animal body, especially through the intestinal wall. The beneficial effect may be, for example, therapeutic, cosmetic or preventative such as prophylactic or contraceptive. The active macromolecular principles can be of natural (biological), synthetic or semi-synthetic origin.

Macromolecules are preferably defined as molecules having a molecular weight of over 1000 Da, preferably over 2000 Da and most preferably over 3000 Da. Examples of macromolecules, including macromolecular active macromolecular principles, include:

1. Polypeptides and proteins such as insulin; calcitonin; human serum albumin; growth hormone; growth hormone releasing factors; galanin; parathyroid hormone; peptide YY; oxyntomodulin; blood clotting proteins such as kinogen, prothombin, fibrinogen, Factor VII, Factor VIII of Factor IX; erythropoeitins and EPO mimetics; colony stimulating factors including GCSF and GMCSF; platelet-derived growth factors; epidermal growth factors; fibroblast growth factors; transforming growth factors; GLP-1; exendin; leptin; GAG; cytokines; insulin-like growth factors; bone- and cartilage-inducing factors; neurotrophic factors; interleukins including IL-1, IL-2, IL-3, IL-4, IL-5, IL-6, IL-7, IL-8, IL-9, IL-10, IL-11, IL-12; interferons including interferon gamma, interferon-1a, interferon alphas; TNF alpha; TNF beta; TGF-beta; cholera toxin A and B fragments; *E. coli* enterotoxin A and B fragments; secretin; enzymes including histone deacetylase, superoxide dismutase, catalase, adenosine deaminase, thymidine kinase, cytosine deaminase, proteases, lipases, carbohydrases, nucleotidases, polymerases, kinases and phosphatases; transport or binding proteins especially those which bind and/or transport a vitamin, metal ion, amino acid or lipid or lipoprotein such as cholesterol ester transfer protein, phospholipid transfer protein, HDL binding protein; connective tissue proteins such as a collagen, elastin or fibronectin; a muscle protein such as actin, myosin, dystrophin, or mini-dystrophin; a neuronal, liver, cardiac, or adipocyte protein; a cytotoxic protein; a cytochrome; a protein which is able to cause replication, growth or differentiation of cells; a signalling molecule such as an intra-cellular signalling protein or an extracellular signalling protein (eg hormone); trophic factors such as BDNF, CNTF, NGF, IGF, GMF, aFGF, bFGF, VEGF, NT3, T3 and HARP; apolipoproteins; antibody molecules; receptors in soluble form such as T-cell receptors and receptors for cytokines, interferons or chemokines; proteins or peptides containing antigenic epitopes and fragments; and derivatives, conjugates and sequence variants of any of the above. These and other proteins may be derived from human, plant, animal, bacterial or fungal sources, and extracted either from natural sources, prepared as recombinants by fermentation or chemically synthesised.

2. Polynucleotides such as long-chain linear or circular single-, double- or triple-stranded DNA, single-, double- or triple-stranded RNA, oligonucleotides such as antisense DNA or RNA, and analogues thereof including PNA and phosphothioate derivates. In one embodiment it is preferred that the polynucleotides used in the invention contain a CpG motif. The coding sequence of the polynucleotide may encode a therapeutic product, in particular the coding sequence may encode an extracellular protein (e.g. a secreted protein); an intracellular protein (e.g. cytosolic, nuclear or membrane protein); a protein present in the cell membrane; a blood protein, such as a clotting protein (e.g. kinogen, prothrombin, fibrinogen factor VII, factor VIII or factor IX); an enzyme, such as a catabolic, anabolic gastrointestinal, metabolic (e.g. glycolysis or Krebs cycle), or a cell signalling enzyme, an enzyme which breaks down or modifies lipids, fatty acids, glycogen, amino acids, proteins, nucleotides, polynucleotides (e.g. DNA or RNA) or carbohydrate (e.g. protease, lipase or carbohydrase), or a protein modifying enzyme, such as an enzyme that adds or takes chemical moieties from a protein (e g a kinase or phosphatase); a transport or binding protein (e.g. which binds and/or transports a vitamin, metal ion, amino acid or lipid, such as cholesterol ester transfer protein, phospholipid transfer protein or an HDL binding protein); a connective tissue protein (e.g. a collagen, elastin or fibronectin); a muscle protein (e.g. actin, myosin, dystrophin or mini-dystrophin); a neuronal, liver, cardiac or adipocyte protein; a cytotoxic protein; a cytochrome; a protein which is able to cause the replication, growth or differentiation of cells; a protein which aids transcription or translation of a gene or regulates transcription or translation (e.g. a transcription factor or a protein that binds a transcription factor or polymerase); a signalling molecule, such as an intracellular or extracellular signalling molecule (e.g. a hormone); an immune system protein such as an antibody, T cell receptor, MHC molecule, cytokine (e.g IL-1, IL-2, IL-3, IL-4, IL-5, IL-6, IL-7, IL-8, IL-9, IL-10, TNF-, TNF-, TGF-), an interferon (e.g. IFN-, IFN-, IFN-), chemokine (e.g. MIP-1, MIP-1, RANTES), an immune receptor (e.g. a receptor for a cytokine, interferon or chemokine, such as a receptor for any of the above-mentioned cytokines, interferons or chemokines) or a cell surface marker (e.g. macrophage, T cell, B cell, NK cell or dendritic cell surfacemarker) (eg. CD 1, 2, 3, 4, 5, 6, 7, 8, 16, 18, 19, 28, 40, or 45; or a natural ligand thereof), a trophic factor (e.g. BDNF, CNTF, NGF, IGF, GMF, aFGF, bFGF, VEGF, NT3, T5, HARP) or an apolipoprotein; a tumour suppressor (e.g. p53, Rb, Rap1A, DCC or k-rev); a suicide protein (thymidine kinase or cytosine deaminase); or a gene repressor. The proteins and peptides encoded by the polynucleotides useful in the invention may be immunogenic i.e. contain an antigen specific to the activity of the protein against which antibodies are generated by the immune system.

The polynucleotide may have control sequences operably linked to the coding sequence. The control sequences may typically be those of any eukaryote or of a virus which infects such eukaryotes. The polynucleotide may comprise an origin of replication.

The polynucleotides may be chemically modified. This may enhance their resistance to nucleases or may enhance their ability to enter cells. For example, phosphorothioate oligonucleotides may be used. Other deoxynucleotide analogs include methylphosphonates, phosphoramidates, phosphorodithioates, N3'P5'-phosphoramidates and oligoribonucleotide phosphorothioates and their 2'-O-alkyl analogs and 2'-O-methylribonucleotide methylphosphonates. Alternatively mixed backbone oligonucleotides (MBOs) may be used. MBOs contain segments of phosphothioate oligodeoxynucleotides and appropriately placed segments of modified oligodeoxy- or oligoribonucleotides. MBOs have segments of phosphorothioate linkages and other segments of other modified oligonucleotides, such as methylphosphonate, which is non-ionic, and very resistant to nucleases or 2'-O-alkyloligoribonucleotides.

The polynucleotide suitable for use in the invention is preferably in a form in which it is substantially free of or associated with cells or with cellular, prokaryotic, eukaryotic, nuclear, chromatin, histone or protein material. It may be in substantially isolated form, or it may be in substantially purified form, in which case it will generally comprise more than 90%, e.g. (more than or at least) 95%, 98% or 99% of the polynucleotide or dry mass in the preparation. Thus the polynucleotide may be in the form of 'naked DNA'.

3. Polysaccharides such as heparin, low-molecular weight heparin, polymannose, cyclodextrins and lipopolysaccharide.

4. Any or all of the above either separately or in combination with each other (for example in the form of a heteroconjugate), or with additional agents.

In preferred embodiments of the invention the active macromolecular principle to be absorbed is selected from calcitonins, insulin, low molecular weight heparin, erythropoeitin, colony stimulating factor, including granulocyte colony stimulating factor (GCSF) and granulocyte monocyte colony stimulating factor (GMCSF), interferons, C-peptide, glucagons-like protein 1 (GLP-1), human growth hormone and parathyroid hormone and analogues and fragments thereof.

In the compositions of the invention, the aromatic alcohol absorption enhancer is present in an amount (by weight) greater than or equal to that of the active macromolecular principle. This provides an effective concentration of aromatic alcohol absorption enhancer at the intestinal cell barrier layer (intestinal wall) so as to cause enhanced absorption in the co-presence of a suitable amount of the active macromolecular principle which, when absorbed, will exert its normal beneficial effect. The amounts of the aromatic alcohol absorption enhancer and active macromolecular principle are readily selected on the basis of the amount (for example, blood concentration level) of the active macromolecular principle concerned which is necessary for therapeutic efficacy. The weight ratio of aromatic alcohol absorption enhancer to active macromolecular principle in the mixture contained in the capsule is suitably at least 1:1, preferably at least 5:1, for example from 1:1 to 100:1, preferably from 3:1 to 50:1, most preferably from 5:1 to 20:1.

The ratio of biguanide to aromatic alcohol absorption enhancer is suitably at least 2:1 by weight, preferably from 2:1 to 10:1, and most preferably from 2:1 to 5:1.

The absolute amount of the active macromolecular principle would be selected on the basis of the dosage of the substance required to exert the normal beneficial effect with respect to the dosage regimen used and the patient concerned. Determination of these amounts falls within the mantle of the practitioner of the invention.

In the composition for oral administration it is preferred that the contents of the capsule comprises a suitable amount of the active macromolecular principle to achieve its normal therapeutic effect. For example, the composition may contain from 0.05 to 50%, preferably from 0.1 to 25%, more preferably from 0.1 to 10% by weight of the active macromolecular principle based on the weight of the capsule contents (not including the capsule itself).

The composition of the invention may further comprise one or more other absorption enhancer compounds, for example, medium chain fatty acids and medium chain monoglycerides.

The composition of the invention may optionally further comprise any conventional additive used in the formulation of pharmaceutical products including, for example, antioxidants, anti-microbials, suspending agents, fillers, diluents, disintegrants, swelling agents, viscosity regulators, plasticisers and acidity regulators (particularly those adjusting the intestinal milieu to between 7 and 7.5) and protease inhibitors such as aprotinin, soybean trypsin inhibitor or gabexate mesylate.

The composition of the invention may optionally further comprise additional active principles which may enhance the desired action of the composition in a synergistic fashion. For example, where the active macromolecular principle is insulin, the composition may also comprise an insulin sensitiser capable of increasing the body's response to the insulin absorbed. Examples of sensitisers which could be employed in this fashion are troglitazone, pioglitazone, rosiglitazone and other members of the glitazone class of molecules.

In the composition of the invention where the mixture is contained in a capsule or tablet that comprises the aromatic alcohol absorption enhancer and active macromolecular principle, the formulation is preferably substantially anhydrous. In more preferred embodiments of the invention the entire composition is substantially anhydrous. Substantially anhydrous in the context of this invention means less than 5%, preferably less than 1% and more preferably less than 0.5% water by weight of the mixture.

The compositions of the invention can, depending on the active macromolecular principle used therein, be used in the treatment of a variety of conditions and diseases of the human or animal body by therapy or, alternately, can be used to introduce macromolecules essential for the diagnosis of diseases and conditions within the human or animal body. The compositions of the invention are preferably pharmaceutical or cosmetic compositions.

The pharmaceutical compositions of the invention are particularly useful in the treatment of diabetes when the composition may comprise insulin, C-peptide or GLP-1 or a mixture thereof as active principle, in the treatment of osteoporosis when the composition may comprise calcitonin or PTH or a mixture thereof, in the treatment of osteoarthritis, when the composition may comprise calcitonin, in the treatment of obesity, where the composition may comprise peptide YY or oxyntomodulin or a mixture thereof, or in the treatment of cancer, where the composition may comprise erythropoetin, GCSF, GMCSF or a mixture thereof.

In the compositions of the invention the mixture contained in the capsule may be a liquid, semi-solid or gel, which is either in the form of a solution or a microparticulate dispersion. That is to say the active macromolecular principle(s) for absorption are incorporated into the formulation either in the form of a solution or as a microparticulate dispersion. Alternatively, the composition may be in the form of a solid.

The compositions of the invention are suitably produced by preparing a substantially anhydrous mixture of the active macromolecular principle and the aromatic alcohol absorption enhancer and then optionally filling uncoated capsules with the mixture and optionally coating them with an appropriate polymer mixture to achieve the desired permeability properties.

Depending on the nature of additional excipients employed, the pharmaceutical composition of the invention may be in liquid, solid, semi-solid or gel form. The pharmaceutical composition of the invention is suitable for administration via any route giving access to different mucosal tissues such as buccal and sublingual mucosa, the nasal palate, the lungs, the rectum, the intestinal tract (including the large and small intestines) and the vagina. In the case of liquid, semi-solid or gel formulations, these may be either anhydrous or aqueous.

Where the intended site of action of the composition of the invention is the intestine, it is desirable that the composition is enclosed within an enteric coating which can withstand the stomach, so that the components of the formulation remain together, undiluted and in close association until they reach the tissues of the small intestine or colon. Such formulations will suitably be anhydrous. Compositions in liquid form will suitably be administered as enteric-coated capsules, while solid formulations may be administered either within enteric-coated capsules, or in tablet form.

The enteric coating is chosen appropriately to withstand the natural condition of the stomach and to become permeable at the desired location in the intestine. This is preferably determined by the pH conditions which modulate along the length of the intestine. Where the site of action is the small intestine, it is preferred that the enteric coating becomes permeable and releases its contents at a pH from 3 to 7, preferably from 5.5 to 7, more preferably from 5.5 to 6.5. Where the intended site of action is the colon, it is preferred that the enteric coating becomes permeable and releases its contents at a pH of 6.8 or above.

Suitable enteric coatings are well known in the art and include polymethacrylates such as those selected from the L and S series of Eudragits in particular Eudragits L12.5P, L12.5, L100, L100-55, L30 D-55, 512.5P, S12.5 and S100. Selection of an appropriate coating for the capsule, which is preferably a gelatine capsule, can readily be made by the person skilled in the art based on their knowledge and the available literature supporting the Eudragit products.

Where the intended site of action is the nasal mucosa, the formulation may be in the form of an aqueous solution or as a dry powder, which can be administered as a spray.

Where the intended site of action is the rectum, an appropriate method of administration is as an anhydrous liquid or solid enclosed within a capsular shell, or incorporated into the matrix of an erodible suppository.

For vaginal application, administration of the formulation in gel form is also

The following Examples serve to illustrate the present invention and should not be construed as limiting.

EXAMPLES

Example 1 Preparation of a Formulation Containing Metformin and Propyl Gallate

To 1 g metformin 1.83 g of distilled water is added. The mixture is then warmed up at approximately 60° C. with gentle shaking until all solid has dissolved. To the clear solution 250 mg of propyl gallate is added. The mixture is then warmed up at approximately 60° C. with gentle shaking until all solid has dissolved. The pH is adjusted to 5.5 by addition of approximately 25 ul of sodium hydroxide. A homogenous solution is obtained which remains clear at room temperature.

Example 2 Preparation of a Formulation Containing Phenformin and Propyl Gallate

A phenformin/propyl gallate formulation is prepared as described in example 1 except that metformin is replaced with phenformin. A homogenous solution is obtained which remains clear at room temperature.

Example 3 Preparation of a Formulation Containing Chlorhexidine Digluconate and Propyl Gallate Chlorhexidine digluconate solution at 200 mg/ml is diluted 2× with distilled water giving solution of 100 mg/ml. To 10 ml of this solution 250 mg of propyl gallate is added. The mixture is then warmed up at approximately 60° C. with gentle shaking until all solid has dissolved. The pH is adjusted to 5.5 by addition of approximately 25 ul of 1M sodium hydroxide. A homogenous solution is obtained which remains clear at room temperature.

Example 4 Preparation of a Formulation Containing Metformin and Butylated Hydroxy Toluene (BHT)

To 400 mg metformin 4.0 g of distilled water is added. The mixture is then warmed up at approximately 70° C. with gentle shaking until all solid has dissolved. To the clear solution 40 mg of BHT is added. The mixture is then warmed up at approximately 70° C. with gentle shaking until all solid has dissolved. A homogenous solution is obtained which remains clear at room temperature.

Example 5 Preparation of a Formulation Containing Phenformin and Butylated Hydroxy Toluene (BHT)

To 400 mg phenformin 4.0 g of distilled water is added. The mixture is then warmed up at approximately 70° C. with gentle shaking until all solid has dissolved. To the clear solution 100 mg of BHT is added. The mixture is then warmed up at approximately 70° C. with gentle shaking until all solid has dissolved. A homogenous solution is obtained which remains clear at room temperature.

Example 6 Preparation of a Formulation Containing Phenformin and Butylated Hydroxy Anisole (BHA)

The preparation method for the Metformin/BHT formulation is as described in example 5 except that BHT is replaced with BHA. A homogenous solution is obtained which remains clear at room temperature.

Example 7 Preparation of a Formulation Containing Metformin, Propyl Gallate and Insulin The metformin/propyl gallate solution is prepared as described in Example 1. The obtained solution is then cooled down to 37° C. and 28.1 mg of insulin is added. The mixture is then incubated at 37° C. with mixing till the insulin is completely dissolved. The solution is then frozen rapidly at −20° C., incubated further at −20° C. for 1 hour and then freeze-dried overnight, by exposing to vacuum of 1 mbar. The dry powder cake is then passed through a sieve so a fine powder is obtained.

Example 8 Dissolution of a Formulation Containing Metformin, Propyl Gallate and Insulin 244 mg of the Metformin/PG/Insulin powder is weighed into an 8 ml vial that is then transferred into a 37° C. water bath. 1 ml of simulated intestinal fluid pH 5.5 pre-warmed to 37° C. is introduced to the sample that is then incubated at 37° C. The powder dissolves within 10 minutes. 100 ul of the solution is transferred to a well of the microplate and the absorbance is measured at 620 nm and 492 nm. The optical density of the solutions is similar to that for simulated intestinal fluid alone, demonstrating that the solution is clear and free from particles, and no scattering is observed.

| Sample | Absorbance at 492 nm | Absorbance at 620 nm |
| --- | --- | --- |
| Powder | 0.064 | 0.038 |
| Intestinal fluid | 0.038 | 0.043 |

Example 9 In Vivo Efficacy of Metformin Hydrochloride/Propyl Gallate/Insulin Mixture in Juvenile Pigs Formulations as prepared in example 7 are mixed with swelling agent and glidant, and the dry powder is filled into capsules, each having components in the proportions shown below. Formulations containing chenodeoxycholate instead of metformin, and salmon calcintonin instead of insulin are prepared for comparison. All formulations have identical amounts of propyl gallate per capsule.

|  | 41B | 90A | 88E |
| --- | --- | --- | --- |
| Insulin | 3.75 mg | 3.75 mg |  |
| Calcitonin |  |  | 1.00 mg |
| Metformin |  | 133.4 mg | 133.4 mg |
| Chenodeoxycholate | 70.60 mg |  |  |
| Propyl gallate | 33.35 mg | 33.35 mg | 33.35 mg |
| Sodium starch glycolate | 9.69 mg | 15.15 mg | 15.15 mg |
| Fumed silica | 1.08 mg | 1.67 mg | 1.67 mg |
| Soybean trypsin inhibitor |  |  | 10.00 mg |

The capsules are administered in capsules via a stoma into the jejunum of eight juvenile pigs (each ~40 kg weight). Blood glucose levels are measured at intervals over a six hour period and mean change in AUC of plasma glucose is calculated in h·mmol/l. As can be seen from the summary of data below, the formulation containing the metformin/propyl gallate combination displays efficacy equal to or greater than that of chenodeoxycholate/propyl gallate.

|  |  | AUC of change in plasma glucose after 6 hours (h · mmol/l) |
| --- | --- | --- |
| 41B | Insulin/Cheno/PG | −2.25 |
| 90A | Insulin/metformin/PG | −4.02 |
| 88E | Calcitonin/metformin/PG + SBTI (−ve control) | −0.21 |

Example 10 In Vivo Efficacy of Metformin Hydrochloride/Propyl Gallate/Calcitonin Mixture in Juvenile Pigs Formulations as prepared in example 9 (containing 6000 iu salmon calcitonin, 133 mg metformin hydrochloride and 33 mg propyl gallate or 6000 iu salmon calcitonin and metformin hydrochloride alone) are administered as dry powders inside capsules via a stoma into the jejunum of eight juvenile pigs (each ~40 kg weight). Compositions of the contents of each capsule are shown in the table below. Formulations containing chenodeoxycholate are included for comparison.

|  | 90A | 81A | 81B | 82A | 82B | 84A | 84B |
| --- | --- | --- | --- | --- | --- | --- | --- |
| Calcitonin |  | 1 mg | 1 mg | 1 mg | 1 mg | 1 mg | 1 mg |
| Insulin | 3.75 mg |  |  |  |  |  |  |
| Metformin | 133.4 mg |  |  | 133.4 mg | 133.4 mg | 133.4 mg | 133.4 mg |
| Chenodeoxycholate |  | 70.6 mg | 70.6 mg |  |  |  |  |
| Propyl gallate | 33.35 mg | 33.35 mg | 33.35 mg | 33.35 mg | 33.35 mg |  |  |
| Sodium starch glycolate | 15.15 mg | 9.45 mg | 9.45 mg | 15.15 mg | 15.15 mg | 15.15 mg | 15.15 mg |
| Fumed silica | 1.67 mg | 1.05 mg | 1.05 mg | 1.67 mg | 1.67 mg | 1.67 mg | 1.67 mg |

-continued

|  | 90A | 81A | 81B | 82A | 82B | 84A | 84B |
|---|---|---|---|---|---|---|---|
| Soybean trypsin inhibitor |  |  | 10.00 mg |  | 10.00 mg |  |  |
| Aprotinin |  |  |  |  | 10.00 mg |  | 10.00 mg |

Blood calcium levels are measured at intervals over a six hour period and mean change in AUC of plasma calcium is calculated in h·mmol/l. As can be seen from the summary of data below, calcium levels are reduced below the baseline as a result of introduction of calcitonin into the bloodstream from the intestine. The metformin/PG combination is most efficacious, more so than the metformin in the absence of PG, indicating that the absorbtion enhancing effect is not due to metformin itself, but is the result of action of the propyl gallate, whose dissolution in aqueous media in the gut is brought about by the presence of the metformin. Further enhancement of activity can be brought about by inclusion of protease inhibitors in the formulations.

|  |  | AUC of change in plasma calcium after 6 hour (h · mmol/l) |
|---|---|---|
| 90A | Insulin/metformin/PG (−ve control) | −0.51 |
| 81A | Calcitonin/chenodeoxycholate/PG | −0.89 |
| 81B | Calcitonin/chenodeoxycholate/PG + SBTI | −1.43 |
| 82A | Calcitonin/Metformin/PG | −1.12 |
| 82B | Calcitonin/Metformin/PG + aprotinin | −2.04 |
| 84A | Calcitonin/Metformin - no PG | −0.65 |
| 84B | Calcitonin/Metformin + aprotinin - no PG | −0.68 |

Example 11 In Vivo Efficacy of Metformin Hydrochloride/Propyl Gallate/Calcitonin Mixture in Juvenile Pigs A formulation as prepared in example 9 (each capsule containing 4 mg parathyroid hormone, 133.4 mg metformin hydrochloride, 33.35 mg propyl gallate, 15.15 mg sodium starch glycolate, 1.65 mg fumed silica and 10.00 mg soybean trypsin inhibitor) is administered via a stoma into the jejunum of eight juvenile pigs (each ~40 kg weight). Blood calcium levels are measured at intervals over a six hour period. As can be seen from the data below, calcium levels are changed from the baseline as a result of introduction of PTH into the bloodstream from the intestine.

|  |  | Peak-to-trough difference in plasma calcium (mmol/l) |
|---|---|---|
|  | PTH solution in buffered saline s.c (0.4 mg) | 0.31 |
| 88B | PTH in Metformin/PG formulation i.j. (4.0 mg) | 0.27 |

The invention claimed is:

1. A method of enhancing the absorption of an active macromolecular principle in a patient, which method comprises administering to the patient a composition comprising:
   an aromatic alcohol selected from the group consisting of propyl gallate, an analogue thereof and a derivative thereof,
   a dissolution aid which enhances the solubility of the aromatic alcohol in an aqueous medium wherein the dissolution aid is a biguanide or a pharmaceutically acceptable salt thereof and wherein the biguanide or pharmaceutically acceptable salt thereof is in an amount of from at least 94 mg to 178 mg per dose of the composition; and
   the active macromolecular principle;
   wherein the weight ratio of biguanide to aromatic alcohol is 2:1 to 10:1 wt/wt.

2. A method according to claim 1, wherein the active macromolecular principle to be absorbed is selected from the group consisting of a polypeptide, a protein, a polynucleotide, a polysaccharide and a mixture thereof.

3. A method according to claim 2, wherein the active macromolecular principle to be absorbed is selected from the group consisting of calcitonin, insulin, low molecular weight heparin, erythropoietin, granulocyte colony stimulating factor, interferon, C-peptide, GLP-1, human growth hormone, parathyroid hormone, an analogue thereof and a fragment thereof.

4. A method according to claim 3, wherein the active macromolecular principle to be absorbed is selected from the group consisting of insulin, calcitonin, parathyroid hormone, an analogue thereof, and a fragment thereof.

5. A method according to claim 4, wherein the active macromolecular principle to be absorbed is insulin, an analogue thereof, or a fragment thereof.

6. A method of enhancing the absorption of an active macromolecular principle in a patient, which method comprises administering to said patient a composition comprising:
   (a) an active macromolecular principle,
   (b) an aromatic alcohol absorption enhancer which is selected from the group consisting of propyl gallate, an analogue thereof and a derivative thereof,
   a dissolution aid which enhances the solubility of the aromatic alcohol absorption enhancer in an aqueous medium wherein the dissolution aid is a biguanide or a pharmaceutically acceptable salt thereof and wherein the biguanide or pharmaceutically acceptable salt thereof is in an amount of from at least 94 mg to 178 mg per dose of the composition; and
   wherein the aromatic alcohol absorption enhancer is present in an amount by weight greater than or equal to that of the active macromolecular principle, and
   wherein the weight ratio of biguanide to aromatic alcohol is 2:1 wt/wt to 10:1 wt/wt.

7. A method according to claim 6, wherein the composition comprises less than 5% by weight water.

8. A method according to claim 6, wherein the composition is a solution, a micro-particulate dispersion or a solid.

9. A method according to claim 6,
   wherein the active macromolecular principle is selected from the group consisting of insulin, C-peptide, GLP-1, and a mixture thereof; and
   wherein the method is for treating diabetes.

10. A method according to claim 6,
wherein the active macromolecular principle is calcitonin or PTH; and
wherein the patient has osteoporosis.

11. A method according to claim 6,
wherein the active macromolecular principle is calcitonin; and
wherein the patient has osteoarthritis.

12. A method according to claim 6,
wherein the active macromolecular principle is selected from the group consisting of peptide YY, oxyntomodulin and a mixture thereof; and
wherein the patient has obesity.

13. A method according to claim 6, wherein the active macromolecular principle is selected from the group consisting of erythropoietin, granulocyte-colony stimulating factor (GCSF), granulocyte-macrophage colony stimulating factor (GMCSF) and a mixture thereof; and
wherein the patient has cancer.

14. The method of claim 1, wherein the biguanide is present in an amount of about 50% to about 90% by weight of the composition.

15. The method of claim 14 wherein the aromatic alcohol is present in an amount from 5% to 30% by weight of the composition.

16. The method of claim 6, wherein the biguanide is present in an amount of about 50% to about 90% by weight of the composition.

17. The method of claim 16, wherein the aromatic alcohol is present in an amount from 5% to 30% by weight of the composition.

* * * * *